United States Patent [19]

Van Bochove et al.

[11] Patent Number: 4,494,410
[45] Date of Patent: Jan. 22, 1985

[54] CONVERTOR APPARATUS FOR ACCURATE AND CONSISTENT NON-DESTRUCTIVE TESTING OF OBJECTS

[75] Inventors: Gijsbertus F. J. Van Bochove, Vlaardingen; Petrus A. A. M. Somers, Alphen A/D Rijn, both of Netherlands

[73] Assignee: Fokker B.V., Netherlands

[21] Appl. No.: 466,838

[22] Filed: Feb. 16, 1983

[30] Foreign Application Priority Data

Feb. 16, 1982 [NL] Netherlands .................... 8200586

[51] Int. Cl.³ ............................................. G01N 29/00
[52] U.S. Cl. ........................................ 73/644; 73/584; 73/588; 310/336
[58] Field of Search .................. 73/584, 588, 644; 310/334, 336

[56] References Cited

U.S. PATENT DOCUMENTS

| | | | |
|---|---|---|---|
| 3,205,702 | 9/1965 | Joy | 310/336 |
| 3,798,961 | 3/1974 | Flambard et al. | 73/644 |
| 3,883,841 | 5/1975 | Norel et al. | 310/336 |
| 4,242,744 | 12/1980 | Rottmar | 73/644 |

Primary Examiner—Howard A. Birmiel
Attorney, Agent, or Firm—Handal & Morofsky

[57] ABSTRACT

The invention relates to a convertor for converting electrical vibrations into mechanical vibrations for non-destructive testing of objects, in particular bonded joints between two or more sheets or between sheets and a honey comb structure. Said convertor comprises a polycrystalline, piezo-electric disc, with mutually insulated electrodes on both head faces. The disc is secured in a supporting element by a suspension with a resilient member pressing centrally through a metal pin against the internal head face of the disc. The supporting element is movably installed into a holder such that the supporting element can be moved from a retracted position in the direction of the extended position until such a position is reached that the piezo-electrical disc is pressured against the object to be tested with a predetermined force.

The invention also relates to a method for using the convertor.

15 Claims, 1 Drawing Figure

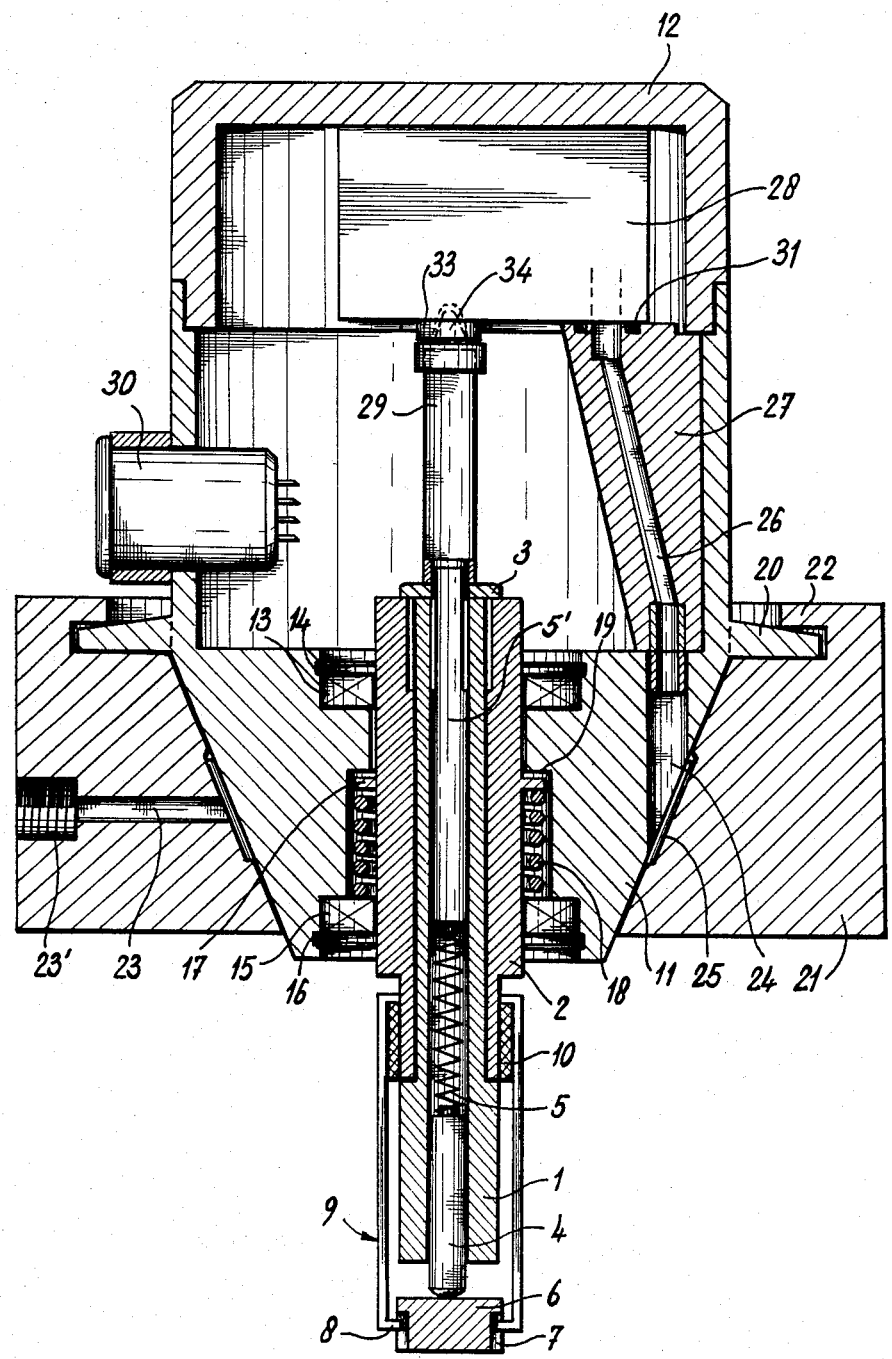

CONVERTOR APPARATUS FOR ACCURATE AND CONSISTENT NON-DESTRUCTIVE TESTING OF OBJECTS

The invention relates to a convertor for converting electrical vibrations into mechanical vibrations for non-destructive testing of objects, more particular bonded joints between two or more sheets or between sheets and a honey comb structure, using a poly crystalline, piezo-electric disc. The disc is provided with mutually insulated electrodes on its two head faces and is through a suspension secured into a supporting element. The supporting element is provided with a resilient member pressing centrally through a metallic pin against one head face of the disc.

Such a convertor is disclosed in the Dutch Pat. No. 101,143 and U.S. Pat. No. 3,119,254. This convertor is particularly designed to be hand held onto the surface of the object to be tested. The object to be tested can for instance comprise a bonded layer structure in which the quality of the bonding has to be checked by means of the convertor. For that purpose the convertor is placed onto the surface by hand and pressed thereon such that the extremities of a plurality of metallic tongues, belonging to the suspension of the piezo-electric disc in this known convertor extending through a plurality of grooves of the piezo-electric disc, will be released from the ends of said grooves such, that the piezo-electric disc is able to perform a vibration which is not interfered by the suspension.

The two electrodes of the piezo-electric disc are during operation connected to a frequency sweep generator. After the convertor is positioned onto the object to be tested in the above mentioned way said frequency sweep generator will supply an electrical signal, to the piezo-electric disc, the signal varying in a preselected frequency range. That will cause the piezo-electric disc to perform a mechanical vibration. At some frequency the disc will start resonating. Said resonant frequency and the damping of the vibration performed by the disc substantially depends on the spring constant of the bonded structure lying underneath the object to be tested, and said spring constant depends on the quality of the bonded joints of the object to be tested. To obtain a good transfer of the mechanical vibrations between the piezo-electric disc and the object to be tested, the surface of the object to be tested is first wetted with transmitting liquid, for instance a suitable oil, by means of a brushlet.

The lowest force, for pressing the known convertor onto the object to release the piezo-electric disc from the extremities of the metallic tongues, is determined by the bias of the spring pressing the metallic pin against the piezo-electric disc in the non-activated position. The maximum press-on force depends on the stiffness of said spring. Because the convertor is pressed against the object to be tested by hand, said press-on force will even with skilled personal not be reproducible. Anyhow this will influence the damping of the resonant vibration of the piezo-electric disc. Furthermore both the resonant frequency and the damping of the resonance vibration of the convertor will be influenced when the convertor is pressed somewhat sloping against the object to be tested. Because of the fact that the press-on force is not reproducible and the convertor is not pressed against the object to be tested exactly perpendicular in most cases, unwanted deviations will occur in the resulting measurement. It is even possible that an operator shifts the initial measured damping of the resonant frequency in the direction of the desired value by more or less pressing or more or less sloping the convertor achieving a different measured result not corresponding to the facts.

Furthermore the measurement will be influenced by the thickness of the layer of transmitting liquid present between the convertor and the object to be tested. It is clear that even operators with some experience in handling the convertor will not always supply a layer of liquid with the same thickness.

Also the time period between the positioning of the convertor and the read out of the measured result influences the measurement because of transitional phenomena.

The invention is aimed at improving a convertor of the kind mentioned above by addresing the above mentioned points.

This objective is met by a convertor of the kind mentioned above, in that the supporting element is supported to move in the direction perpendicular to the object to be tested between a retracted and a extended position in a holder forming a part of an arm of a positioning unit, such that at least the piezo-electric disc projects in every position from this holder. The supporting element is biassed in and retracted non activated position, the is brought a short distance from the object to be tested by said arm. The holder is provided with a drive means for moving the supporting element from the retracted position in the direction of the extended position until such a position is reached that the piezo-electric disc is pressed against the object to be tested with a predetermined force which is adjustable by a control unit.

The invention will now be explained in more detail with reference to an embodiment shown in the FIGURE.

In the FIGURE the reference number 1 refers to an inner sleeve of insulating material, which is mounted in an outer sleeve 2 by means of a lock-nut 3, which is screwed on top of the inner sleeve 1. In said inner sleeve 1 a metal pin 4 is placed, which is pressed against a piezo-electric disc 6 by a spring 5. This spring 5 rests at the other side against a rod 5′ which is adjustably screwed in the inner sleeve 2 and with which the bias of spring 5 can be adjusted. The piezo-electric disc 6 carries at the internal head surface a first metal electrode, which is electrical in contact with metal pin 4, and carries at the external head surface a second metal electrode. In the illustrated embodiment the disc 6 is provided with a number of longitudinal grooves 7 in the cylindrical surface terminating at some distance from the internal head surface of disc 6. The metallization of the external head surface is continued in the grooves throughout the whole length thereof. These grooves receive a plurality of extremities 8 of a plurality of metallic tongues 9 which are directed to the cylindrical surface of the disc 6, and a plurality of upper extremities of said tongues are connected to outer sleeve 2 by a ring 10 in a way not indicated in detail.

This entire combination, which is above indicated by the term "supporting element" is supported in a holder that permits the supporting element to be displaced along its major axis. The holder comprises a cylindrical part 11 and a sealing cap 12. The cylindrical part 11 is provided with a stepped continuous bore, which is divided in the FIGURE from the top to the bottom in a first upper section with comparatively large diameter, a second section with a smaller diameter designed for receiving a bearing 13, which is locked by a spring ring 14, a third section with a smaller diameter, a fourth section with a diameter being larger then that of the third section, but smaller than that of a fifth section. The fifth section has a diameter which is equal to in this embodiment the second section's diameter. In said fifth section a second bearing 15 is present which is locked by a second spring ring 16.

As shown in the FIGURE the outer sleeve 2 is provided with a protruding ring 17, which is integrally formed with the outer sleeve 2 and positioned in the fourth section of the bore. In said fourth section also a spring 18 is mounted, which is disposed between ring 17 and bearing 15, and which causes the ring 17 to be pressed against a shoulder 19 between the third and fourth sections of the bore.

The exterior of the cylindrical part 11 is conically shaped, narrowing in a downard direction. The cylindrical part 11 is positioned in a ring member 21, forming a part of a positioning member, not further shown in detail. This ring member 21 is provided with a bore which is also conically shaped such that the conically shaped section of part 11 fits therein. The cylindrical part 11 is provided with projecting members 20, engaging under the hooked edge 22 of ring 21, such that the cylindrical part 11 can be secured in said ring 21 in a known way.

Ring 21 is provided with a bore 23, which can be connected to a conduit, not shown, for supplying a pressurized fluid, for instance pressurized air or hydraulic liquid, through the connector section 23'. Bore 23 opens in a angular recess 25 in the wall of the conical bore in ring 21. The cylindrical part 11 is provided with a vertical bore 24, of which the bottom end opens in said recess 25. The upper end of bore 24 communicates with a bore 26 which is disposed in a supporting element 27. Supporting element 27 is disposed against the inner wall of the upper bore section of the cylindrical part 11. On top of said supporting element 27 a hydraulic or pneumatic unit 28 is positioned, whereby a gasket ring 31 ensures a leakproof connection. This hydraulic or pneumatic unit 28 is provided with a piston 33 of which a part is shown in the FIGURE. This piston 33 presses against a piston rod 29 of which the lower end rests against the upper side of the supporting element 27 through an insulating part 34. If pressure is applied to the pneumatic or hydraulic unit 28 through the connection 23', 23, 25, 24, 26, then the piston rod 29 will be displaced in a downward direction by which the entire supporting unit will be displaced in downward direction. The supporting unit slides in bearings 13 and 15 against the force of biassing spring 18. If the pressure is reduced, biasing spring 18 will return the supporting unit to its initial position in which ring 17 rests against shoulder 19. In the shown embodiment, the hydraulic or pneumatic unit 28 is mounted in head 12.

The device described above is used as follows. The converter according to the invention is positioned at a short distance above the object to be tested by a positioning unit, not shown in the FIGURE, of which ring 21 is a part. Then a dosed quantity of contacting liquid is sprayed on said surface at the spot where the piezoelectric disc will be pressed against the surface by a not shown dosing spray device. After a predetermined delay, during which the liquid is permitted to spread out over the surface, the pressure in the pneumatic or hydraulic unit 28 is increased via the described fluid communication system, such that the supporting element, comprising parts 1 to 9 is displaced in an axial direction between bearings 13 and 15, until the piezo-electric disc 6 touches the object to be tested via the contacting liquid sprayed onto the surface. As the movement of piston rod 29 is directed downward, the extremities 8 of the metal tongues 9 will release from the upper extremities of grooves 7 after the piezo-electric disc 6 has contacted the surface through the contacting liquid. This touching of the contacting liquid could be detected as a sudden increase in damping of the vibration performed by the piezo-electric disc. From this moment on the pressure will be controlled such that the piston rod 29 will move over a predetermined distance in a downward direction to press the piezo-electric disc 6 with a predetermined biassing force generated by spring 5 against the object to be tested. Then the convertor is maintained in this position during a predetermined period. This period is required to let eventual transient phenomena fade away. At the end of this period the resonant frequency of the piezo-electric disc 6 as well as the relative strength of the signal from the piezo-electric disc 6 are registered and the convertor is returned to its initial position by a pressure decrease in pressure unit 28. After that, the device is ready for performing the next measurement.

This entire operation of the convertor is controlled by a control unit, which is activated as soon as the positioning unit, not shown, has brought the convertor to a short distance from the object to be tested. Signals are supplied to this control unit from a measuring unit. Said measuring unit receives signals from the piezoelectric disc 6. To transport said signals from the convertor an electrical connector 30 is mounted in the wall of the cylindrical section 11 at the level of the first part of the bore or in the cap 12. Through this connector 30 signals from the piezo-electric disc 6 are supplied to a measuring device, not shown. As soon as this measuring device detects from a change in damping, that the piezo-electric disc is making contact with the object to be tested, the control unit causes the pressure supplied to the pneumatic or hydraulic pressuring unit 28 to increase with a predetermined value, such that the supporting element will be displaced over a predetermined distance in an axial direction. Then the measuring unit measures a delay period and at the end of this period the desired values are recorded.

It is clear that the illustrated embodiment of the invention only comprises an example, and said example can be modified in several ways within the scope of the invention.

It is, for instance, possible to place a pressure sensor between spring 5 and pin 5'. The control unit then causes the pressure in the hydraulic or pneumatic unit 28 to increase until the pressure sensor indicates the piezo-electric disc is pressed against the surface of the object to be tested with a predetermined force. If the bias of spring 5 is, in the rest position, substantially lower than this predetermined press-on force, then it is guaranteed that during the measurement, the extremities of the tongues are released from the upper edges of the grooves in the piezo-electric disc 6.

In the embodiment described above a pneumatic or hydraulic unit is used, which can be single acting, i.e., it has only to exert a force in the downward direction because spring 18 provides a force in the reverse direction. However it is also possible to use a double acting pneumatic or hydraulic unit 28, where the return spring can be omitted and piston rod 29 has to be directly connected to piston 33.

It is further possible to use a field coil cooperating with an armature which is secured at the upper side of the supporting element instead of a hydraulic or a pneumatic unit 28. This armature can for instance be embodied as a rod extending vertically above the supporting element instead of the piston rod 29, shown in the FIGURE. The field coil can comprise a solenoid, positioned around said armature outside the casing formed by the cylindrical part 11 and sealing cap 12. By controlling the current through this coil the armature can be moved over a larger or a smaller distance against the force of the spring.

Also the invention is not limited to the embodiment of the suspension of the piezo-electric disc 6, shown in the FIGURE.

Hence the above described embodiment of the invention only serves as an example without limiting the invention thereto.

We claim:

1. A convertor for converting electrical vibrations into mechanical vibrations for non-destructive testing of objects, in particular, bonded joints between a plurality of sheets or between sheets and a honey comb structure, comprising a polycrystalline, piezo-electric member, which is provided with mutually insulated electrodes on its first and second head faces, said member being suspended and secured into a supporting element, said supporting element being provided with a resilient member pressing centrally through a metal pin against the first head face of said member said supporting element being supported in a holder and mounted for movement with respect to said holder in a direction perpendicular to the object to be tested between a retracted rest position and an extended position, said holder forming a part of an arm of a positioning unit, said supporting element being supported such that the piezo-electric member extends from said holder, said supporting element being biassed in the retracted rest position, said arm being adapted to move said supporting element brought to a point that is a short distance from the object to be tested, said arm and holder being provided with drive means for moving the supporting element from the retracted rest position, in a direction toward the extended position, to a position where the piezo-electric member is pressed against the object to be tested with a predetermined force in response to a control unit.

2. A convertor according to claim 1, wherein said drive means comprises a double acting fluidic motor having a piston/cylinder unit, whose piston rod is connected to the upper side of the supporting element.

3. A convertor according to claim 1, wherein said drive means comprises a single acting fluidic motor having a piston/cylinder unit, of which the piston presses against a piston rod, which is connected to the upper side of the supporting element, and the supporting element is biassed in the retracted rest position by a spring, which said spring engages both the supporting element and the holder.

4. A convertor according to claim 1, wherein said drive means comprises an electrical field coil and an armature cooperating therewith, which drive means is connected to the supporting element.

5. A convertor according to claim 1, wherein said drive means is controlled by the control unit, and signals from the convertor are supplied to measuring device; said measuring device causes the piezo-electric member to vibrate by means of variable frequency signal.

6. A convertor according to claim 5, wherein said control unit is connected with the measuring device, and the control unit is supplied with signals from the measuring device at the moment the piezo-electric member contacts the object to be tested.

7. A convertor according to claim 5, wherein between the extremity of the resilient member and the supporting element a pressure sensor is mounted for measuring the force by which the piezo-electric disc is pressed against the object to be tested.

8. A convertor as in claim 1, wherein said supporting element is mounted in a supporting structure in said holder, said supporting structure comprising a peripheral support surface which faces a facing peripheral support surface on an engagement member secured to the outside of said supporting element, and wherein said supporting element is urged into said retracted rest position by a resilient member which resiliently engages said peripheral support surface and said facing peripheral support surface.

9. A convertor as in claim 8, wherein said drive means comprises a rod which engages said supporting element.

10. A convertor as in claim 9, wherein said drive means further comprises a fluidic motor connected to said rod.

11. A convertor as in claim 10, wherein said fluidic motor is configured as a hydraulic piston and cylinder device.

12. A convertor as in claim 10, wherein said fluidic motor is configured as a pneumatic piston and cylinder device.

13. A convertor as in claim 9, wherein said drive means further comprises an electric field coil and an armature cooperating therewith, said armature which engages said supporting element.

14. A convertor as in claim 1, wherein said piezo-electric member further comprises a peripheral surface disposed between said first and second headface, said peripheral surface defines a plurality of grooves extending from said first headface, the electrode associated with said first headface extends throughout said grooves.

15. An improved convertor apparatus, for converting electrical vibrations into mechanical vibrations for non-destructive testing of objects, comprising:
    (a) a polycrystalline piezo-electric member having first and second endfaces and a peripheral surface disposed between said endfaces, said peripheral surface defining a plurality of grooves extending from said first endface;
    (b) first and second mututally insulated electrodes disposed on said first and second endfaces, said first electrode extending from said first endface into said grooves;
    (c) a plurality of conductive tongues, one of said tongues disposed in each of said grooves and positioned peripherally about said piezo-electric member;
    (d) a first conductive resilient member disposed against said second endface, and making contact with said second electrode;

(e) member means for bearing against said first conductive resilient member to urge it into electrical contact with said second electrode;

(f) mounting means for slidably supporting said first conductive resilient member and said plurality of conductive tongues as one supporting element;

(g) movable arm means for supporting said mounting means at a desired position;

(h) spring means for resiliently urging said supporting element in the direction of said first electrode to a predetermined point and for allowing said supporting element to be resiliently urged in the direction toward said second electrode; and (i) displacement means for urging said mounting means in the direction toward said first electrode in response to a control signal.

* * * * *